(12) United States Patent
Gallagher et al.

(10) Patent No.: US 9,061,029 B2
(45) Date of Patent: Jun. 23, 2015

(54) METHOD OF TREATING PROLIFERATIVE DISORDERS AND OTHER PATHOLOGICAL CONDITIONS MEDIATED BY BCR-ABL, C-KIT, DDR1, DDR2 OR PDGF-R KINASE ACTIVITY

(75) Inventors: Neil Gallagher, Basel (CH); Ophelia Yin, Denville, NJ (US)

(73) Assignee: Novartis AG, Basel (CH)

( * ) Notice: Subject to any disclaimer, the term of this patent is extended or adjusted under 35 U.S.C. 154(b) by 507 days.

(21) Appl. No.: 13/509,626

(22) PCT Filed: Nov. 17, 2010

(86) PCT No.: PCT/US2010/056926
§ 371 (c)(1),
(2), (4) Date: May 14, 2012

(87) PCT Pub. No.: WO2011/062927
PCT Pub. Date: May 26, 2011

(65) Prior Publication Data
US 2012/0289528 A1 Nov. 15, 2012

Related U.S. Application Data

(60) Provisional application No. 61/261,812, filed on Nov. 17, 2009.

(51) Int. Cl.
*A61K 31/506* (2006.01)
*C07D 239/69* (2006.01)
*A61K 9/00* (2006.01)

(52) U.S. Cl.
CPC ............ *A61K 31/506* (2013.01); *C07D 239/69* (2013.01); *A61K 9/0095* (2013.01)

(58) Field of Classification Search
CPC ....... A61K 31/506; A61K 9/00; C07D 239/69
USPC .......................................... 514/275; 544/297
See application file for complete search history.

(56) References Cited

FOREIGN PATENT DOCUMENTS

| KR | 2009/0042398 | 4/2009 |
|---|---|---|
| WO | WO 2004/005281 A1 | 1/2004 |
| WO | 2004/012662 A2 | 12/2004 |
| WO | WO 2006/119154 A1 | 11/2006 |
| WO | 2006135641 A2 | 12/2006 |
| WO | 2007015870 A2 | 2/2007 |
| WO | 2007015871 A1 | 2/2007 |
| WO | 2008037716 A2 | 4/2008 |

OTHER PUBLICATIONS

Hazarika et al., "Tasigna for chronic and accelerated phase Philadelphia chromosome—positive chronic myelogenous leukemia resistant to or intolerant of imatinib", Clinical Cancer Research: An Official Journal of the American Association for Cancer Research, vol. 14, No. 17, pp. 5325-5331, Sep. 1, 2008.

Tanaka et al., "Clinical pharmacokinetics (PK) of AMN107, A Novel Inhibitor of Bcr-Abl, in healthy subjects and patients with imatinib resistant or intolerant chronic myelogenous leukemia (CML) or relapsed/refractory Ph+ acute lymphocytic leukemia (Ph+ALL)", J. Clin. Oncol. 2006 ASCO Annual Meeting Proceedings Part I, vol. 24, No. 18S,pp. 3095, 2006 (Abstract).

Van Erp et al., "Clinical pharmacokinetics of tyrosine kinase inhibitors", Cancer Treatment Reviews, vol. 35, No. 8, pp. 692-706, Sep. 5, 2009.

Yin et al. "Effect of Grapefruit Juice on the Pharmacokinetics of Nilotinib in Healthy Participants", Journal of Clinical Pharmacology, vol. 50, No. 2, pp. 188-194, Feb. 1, 2010.

Yin et al., "Effect of Yogurt and Applesauce on the Oral Biovailability of Nilotinib in Healthy Subjects", Journal of Clinical Pharmacology, vol. 51, No. 9, pp. 1580-1586, 2011.

Allen, et al., Stability of ramipril in water, apple juice, and applesauce; American Journal of Health-System Pharmacy; Issue: vol. 52(21), Nov. 1, 1995, pp. 2433-2436.

Andersson et al., "Esomeprazole 40mg Capsules are Bioequivalent when Administered Intact or as the Contents Mixed with Applesauce"; Clin Drug Invest 2001; 21 (1): 67-71.

Bladh et al., "A New Esomeprazole Packet (Sachet) Formulation for Suspension: In Vitro Characteristics and Comparative Pharmacokinetics Versus Intact Capsules/Tablets in Healthy Volunteers"; Clinical Therapeutics/ vol. 29, No. 4, 2007, 640-649.

Broomhead et al., "Comparative Bioavailability of Sustained-Release Morphine Sulfate Capsules versus Pellets" Clin. Drug Invest. Aug. 1997; 14 (2): 137-145.

Comer et al.; Randomized, Double-Blind Clinical Outcomes, Safety, and Tolerability Study of Pantoprazole Delayed-Release Granules in Children Aged 1 to 5 Years with Endoscopically Proven Symptomatic Gastroesophageal Reflux Disease (GERD); Gastreoenterology, May 2009, vol. 136, No. 5, Suppl. 1., pp. A-444.

(Continued)

*Primary Examiner* — Raymond Henley, III
(74) *Attorney, Agent, or Firm* — Gregory Houghton

(57) ABSTRACT

The present invention relates to a regimen for the administration of a pyrimidylaminobenzamide of formula I

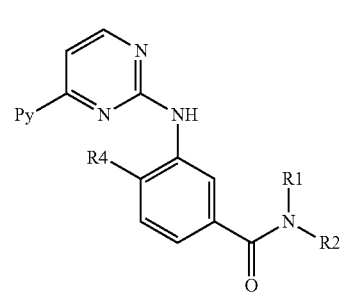

(I)

wherein the radicals as defined herein, or of a pharmaceutically acceptable salt thereof, for the treatment of proliferative disorders, particularly solid and liquid tumors, and other pathological conditions mediated by the Bcr-Abl oncoprotein, the cell transmembrane tyrosine kinase receptor c-Kit, DDR1 (discoidin domain receptor 1), DDR2 (discoidin domain receptor 2) or PDGF-R (platelet derived growth factor receptor) kinase activity, wherein the pyrimidylaminobenzamide of formula I and, optionally, pharmaceutically acceptable carriers, are dispersed in a fruit preparation.

8 Claims, No Drawings

(56) References Cited

OTHER PUBLICATIONS

Eliiot et al., "Pharmacokinetic Evaluation of a Sprinkle-Dose Regimen of a Once-Daily, Extended-Release Morphine Formulation"; Clinical Therapeutics/vol. 24, No. 2, 2002, pp. 260-268.

Isles et al., "Bioavailability of Somophyllin-CRT capsules" br. J. Clin. Pract. 38, No. 9, Suppl. 35, 1984pp. 68-70.

Lee et al., "Effects on the Pharmacokinetics and Pharmacodynamics in the Elderly of Coadministering Ramipril with Water, Apple Juice, and Applesauce"; Pharmaceutical Research, vol. 13, No. 4, 1996, pp. 639-642.

Olsen et al., "Silodosin, an Alpha-Blocker for the Treatment of the Signs and Symptoms of Benign Prostatic Hyperplasia, Can Be Sprinkled on Applesauce Without Effect on Bioavailability"; The Consultant Pharmacist Oct. 2009 vol. 24. No. 10.

Shah et al., "Bioavailability of zonisamide capsule administered as sprinkle in healthy subjects"; Pharmacotherapy, vol. 21, No. 10, pp. 1288, 218, 2001.

Wells et al., "In Vitro Stability, Potency, and Dissolution of Duloxetine Enteric-Coated Pellets After Exposure to Applesauce, Apple Juice, and Chocolate Pudding"; Clinical Therapeutics/ vol. 30, No. 7, 2008, 1300-1308.

Witschital et al., "žPharmakokinetik von Theophyllin in einer Retardformulierung bei jugendlichen Asthmatikern"; Arzneimittel-Forschung (1998), 45 (5a). 593-596.

Broomhead, et al., "Morphine bioavailability and pharmacokinetic comparison of Kadian (sustained release morphine sulfate) capsules and pellets (Sprinkling) in human volunteers under fasted and fed conditions", Proc. Am. Soc. Clin.Oncol. 16, 33 Meet, p. 61a, 1997.

Jarkowski and Sweeney, "Nilotinib: A New Tyrosine Kinase Inhibitor for the Treatment of Chronic Myelogenous Leukemia", Pharmacotherapy, vol. 28, No. 11, pp. 1374-1382, 2008.

The South African Medical Journal, "*Citrus aurantium*—beware of the bitter orange", vol. 98, No. 7, pp. 496, 2008.

Sistla et al., "Powder-in-Bottle Formulation of SU011248. Enabling Rapid Progression into Human Clinical Trials", Drug Development and Industrial Pharmacy, vol. 30, No. 1, pp. 19-25, 2004.

Navid et al., Stability of Sunitinib in Oral Suspension, The Annals of Pharmacotherapy, vol. 42, pp. 962-966, 2008.

Strickley et al., "Pediatric drugs—a review of commercially available oral formulations", Journal of Pharmaceutical Sciences, vol. 97, No. 5, pp. 1731-1774, May 1, 2008.

Manrique et al, "Crushed Tablets: Does the Administration of Food Vehicles and Thickened Fluids to Aid Medication Swallowing Alter Drug Release?", J. Pharm. Sci., pp. 207-219, May 1, 2014; Retrieved from the Internet at URL:http://eprints.qut.edu.au/71945/1/21020-54199-1-PB$_{13}$ Crushing.pdf [retrieved on Jun. 3, 2014].

Maitreyee H. et al., "Tasigna for chronic and accelerated phase Philadelphia Chromosome-positive chronic myelogenous leukemia resistant to or intolerant of imatinib", Clinical Cancer Research, vol. 14, No. 17, pp. 5325-5331, 2008.

Yin et al., "Effects of Yogurt and Applesauce on the Oral Bioavailabilty of Nilotinib in Healthy Volunteers", The Journal of Clinical Pharmacology, vol. 51, No. 11, pp. 1580-1586, Nov. 1, 2011.

Strickley et al., "Pediatric drugs-a review of commercially available oral formulations", Journal of Pharmaceutical Sciences, vol. 97, No. 5, pp. 1731-1774, May 1, 2008.

Manrique et al, "Crushed Tablets: Does the Administration of Food Vehicles and Thickened Fluids to Aid Medication Swallowing Alter Drug Release?", J. Pharm. Sci., pp. 207-219, May 1, 2014; Retrieved from the Internet at URL:http://eprints.qut.edu.au/71945/1/21020-54199-1-PB__Crushing_pdf [retrieved on Jun. 3, 2014].

METHOD OF TREATING PROLIFERATIVE DISORDERS AND OTHER PATHOLOGICAL CONDITIONS MEDIATED BY BCR-ABL, C-KIT, DDR1, DDR2 OR PDGF-R KINASE ACTIVITY

This application is a 371 of PCT/US2010/056926 filed on Nov. 17, 2010, which claims benefit of U.S. Provisional Application No. 61/261,812 filed on Nov. 17, 2009, which in their entirety are herein incorporated by reference.

The present invention relates to a regimen for the administration of a pyrimidylaminobenzamide of formula I

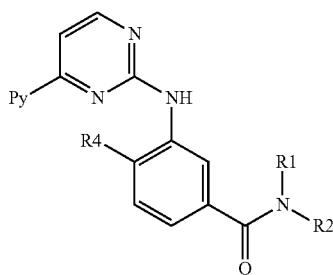

wherein
(a) Py denotes 3-pyridyl,
$R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; and
$R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;
or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;
$R_4$ represents hydrogen, lower alkyl, or halogen;
or
(b) Py denotes 5-pyrimidyl, $R_1$ is hydrogen, $R_2$ is [[(3S)-3-(dimethylamino)-1-pyrrolidinyl]-methyl]-3-(trifluoromethyl)phenyl and $R_4$ is methyl;
or of a pharmaceutically acceptable salt thereof, for the treatment of proliferative disorders, particularly solid and liquid tumors, and other pathological conditions mediated by the Bcr-Abl oncoprotein, the cell transmembrane tyrosine kinase receptor c-Kit, DDR1 (discoidin domain receptor 1), DDR2 (discoidin domain receptor 2) or PDGF-R (platelet derived growth factor receptor) kinase activity.

The compound of formula I, wherein Py denotes 3-pyridyl, $R_1$ represents hydrogen, $R_2$ represents 5-(4-methyl-1H-imidazol-1-yl)-3-(trifluoromethyl)-phenyl and $R_4$ represents methyl, is known under the International Non-proprietary Name "nilotinib". Nilotinib (4-methyl-3-[[4-(3-pyridinyl)-2-pyrimidinyl]amino]-N-[5-(4-methyl-1H-imidazol-1-yl)-3-(trifluoromethyl)-phenyl]benzamide) is approved and marketed in the form of its monohydrochloride monohydrate salt under the brand name Tasigna™. Nilotinib is an ATP-competitive inhibitor for Bcr-Abl and also inhibits c-Kit, DDR1, DDR2 and PDGF-R kinase activity at clinically relevant concentrations. Tasigna™ is available as 200 mg hard gelatin capsule for oral administration for the treatment of Philadelphia-positive chronic myeloid leukaemia (CML) in the chronic phase (CP) and accelerated phase (AP) in patients resistant to or intolerant of at least one prior therapy including imatinib. For the treatment of CML a daily dose of 800 mg of nilotinib is applied in two doses of 400 mg each.

The effect of food on the pharmacokinetic parameters of 400 mg oral dose of nilotinib in the capsule formulation mentioned above was studied in human subjects. The concomitant administration of nilotinib with food significantly increased subjects exposure. In said study the total exposure ($AUC_{0-t}$) was 82% and $C_{max}$ was 112% after a high fat breakfast, whereas the increase in total exposure ($AUC_{0-t}$) was 29% and $C_{max}$ was 55% after a light breakfast given 30 minutes prior to dosing. In view of these findings, it is recommended that nilotinib shall not be taken with a meal in order to minimize the effect of food on nilotinib bioavailability. A statement in this regard is, for instance, included in sections 4.2, 4.4 and 4.5 of the SPC (Summary of Product Characteristics) of the marketing authorization for Tasigna™ issued by the European Medicines Agency (EMEA). Concurrent intake of grapefruit juice also resulted in a modest increase in nilotinib absorption; $C_{max}$ increased by 60% and AUC increased by 29% (Yin O Q, Gallagher N, Li A, et al. *J Clin Pharmacol*. 2010; 50:188-194).

Certain patients, for instance elderly patients and pediatric patients, sometimes have difficulties to swallow hard gelatin capsules as a whole. For those patients, suffering from a proliferative disorder, particularly a solid and liquid tumor disorder, or other pathological conditions mediated by Bcr-Abl, c-Kit, DDR1, DDR2 or PDGF-R kinase activity, an alternative dosage form for nilotinib is required. For pediatric patients also dosage flexibility is desirable in order to allow dosage adjustment in accordance with body weight.

It was now surprisingly found that the problem described above can be resolved by oral administration of nilotinib dispersed in a fruit preparation.

More specifically, as shown in the Examples, a single oral administration of 400 mg nilotinib (contents of two 200 mg nilotinib capsules), each dispersed in one teaspoon of applesauce is bioequivalent to a single oral administration of 400 mg nilotinib given as intact capsules. However, the same amount dispersed in plain non-fat yogurt is not found to be bioequivalent.

Hence, the present invention relates to a method of treating a proliferative disorder or other pathological conditions mediated by Bcr-Abl, c-Kit, DDR1, DDR2 or PDGF-R kinase activity comprising oral administration of an effective dose of a pyrimidylaminobenzamide of formula I

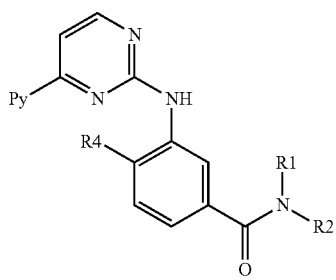

(I)

wherein the radicals have the meanings as provided above, or of a pharmaceutically acceptable salt thereof, and, optionally, other pharmaceutically acceptable carriers, dispersed in a fruit preparation, to a human patient in need thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)$_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic heteroaryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substituents selected from the group defined above as substitutents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)-2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Pyrimidylaminobenzamides within the scope of formula I, wherein py is 3-pyridyl and the process for their manufacture are disclosed in WO 04/005281, which is hereby incorporated into the present application by reference.

The pyrimidylaminobenzamide of formula I wherein Py denotes 5-pyrimidyl, $R_1$ is hydrogen, $R_2$ is [[(3S)-3-(dimethylamino)-1-pyrrolidinyl]methyl]-3-(trifluoromethyl)phenyl and $R_4$ is methyl is also known as INNO-406. The compound, its manufacture and pharmaceutical compositions suitable for its administration are disclosed in EP1533304A.

Pharmaceutically acceptable salts of pyrimidylaminobenzamides of formula I, wherein py is 3-pyridyl, are especially those disclosed in WO2007/015871. In one preferred embodiment nilotinib is employed in the form of its monohydrochloride monohydrate. WO2007/015870 discloses certain polymorphs of nilotinib and pharmaceutically acceptable salts thereof useful for the present invention. A suitable formulation for the administration of nilotinib monohydrochloride monohydrate is described in WO2008/037716.

As used herein, the expression "a proliferative disorder or other pathological conditions mediated by Bcr-Abl, c-Kit, DDR1, DDR2 or PDGF-R kinase activity" activity means melanoma, especially melanoma harboring c-KIT mutations, breast cancer, cancer of the colon, lung cancer, cancer of the prostate or Kaposi's sarcoma, gastrointestinal stromal tumors (GIST), acute myeloid leukemia (AML), leukemia which responds to an inhibition of the Abl tyrosine kinase activity, such as chronic myeloid leukemia (CML) and Philadelphia chromosome positive acute lymphoblastic leukemia (Ph+ ALL), mesothelioma, systemic mastocytosis, hypereosinophilic syndrome (HES), fibrosis, especially hepatic fibrosis and renal fibrosis, rheumatoid arthritis, polyarthritis, scleroderma, lupus erythematosus, graft-versus host diseases, neurofibromatosis, pulmonary hypertension, especially, pulmonary arterial hypertension, Alzheimer's disease, seminomas and dysgerminomas and psoriasis. Preferably, the regime described herein is applied in the following disorders and conditions: GIST, CML, Ph+ ALL, systemic mastocytosis, HES, fibrosis, scleroderma, neurofibromatosis and pulmonary arterial hypertension.

In one embodiment of the present invention the disorder is selected from CML and Ph+ ALL, more preferably CML.

In another embodiment of the present invention the disorder is selected from GIST and melanoma, especially melanoma harboring c-KIT mutations.

In another embodiment of the present invention the disorder is selected from systemic mastocytosis and HES.

In a further embodiment of the present invention the disorder is selected from systemic scleroderma, neurofibromatosis and pulmonary arterial hypertension.

As used herein, the expression "$C_{max}$" means maximum peak concentration in plasma.

As used herein, the expression "AUC" means area under the plasma concentration curve.

The language "oral administration of a pyrimidylaminobenzamide of formula I dispersed in a fruit preparation" as used herein preferably means that the compound of formula I alone or together with at least one suitable pharmaceutical carrier is dispersed in a fruit preparation and administered, preferably manually, to the mouth of the human patient with a suitable device, e.g. a spoon. If desired, 100 to 250 ml of water can be consumed together with the fruit preparation.

As used herein, the term "fruit preparation" means a juice, sauce or puree prepared from fruits, more preferably from apples, peers or peaches, most preferably apples. In one preferred embodiment of the invention, the fruit preparation employed is applesauce. Suitable applesauce is available under the brands Andros® applesauce, Mott's® applesauce and Odenwald Apfelmus (Odenwald-Früchte GmbH, Germany). Grapefruit is known to affect the kinetics of drug up-take in human patients. Hence, the term "fruit preparation" does not encompass any juice, sauce or puree prepared from grapefruit.

For the purposes of the present invention, the total daily dose of nilotinib can be adjusted to the needs of the patients depending, in particular on the disease to be treated and the disease status of the patient under treatment, but in any event will not exceed a total daily dose of 800 mg.

In one embodiment of the invention, the content of two 200 mg nilotinib capsules as disclosed in WO2008/037716 are each dispersed in one teaspoon of applesauce resulting in a single oral administration of 400 mg nilotinib.

Preferably, the mixture of the compound of formula I dispersed in fruit preparation should be taken immediately after its preparation, wherein "immediately" for the purpose of the present invention means within a time frame of 30 minutes, preferably within 15 minutes, more preferably within 5 minutes and most preferably within 2 minutes after preparation.

The present invention further provides a commercial package containing a pyrimidyl-aminobenzamide of formula I, e.g. nilotinib, as defined herein together with instructions to disperse the pyrimidylaminobenzamide of formula I, e.g. nilotinib, in a fruit preparation.

In a further aspect, the instant invention relates to a pyrimidylaminobenzamide of formula I

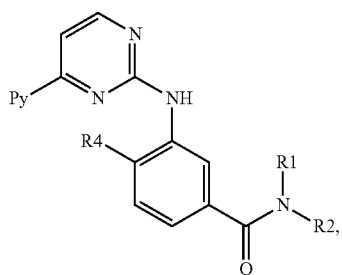

(I)

wherein
(a) Py denotes 3-pyridyl,
$R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; and
$R_3$ represents hydroxy, lower alkoxy, acyloxy, carboxy, lower alkoxycarbonyl, carbamoyl, N-mono- or N,N-di-substituted carbamoyl, amino, mono- or di-substituted amino, cycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; or
$R_1$ and $R_2$, together, represent alkylene with 4, 5 or 6 carbon atoms optionally mono- or di-substituted by lower alkyl, cycloalkyl, heterocyclyl, phenyl, hydroxy, lower alkoxy, amino, mono- or di-substituted amino, oxo, pyridyl, pyrazinyl or pyrimidinyl; benzalkylene with 4 or 5 carbon atoms; oxaalkylene with 1 oxygen and 3 or 4 carbon atoms; or azaalkylene with 1 nitrogen and 3 or 4 carbon atoms, wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N, N-di-substituted carbamoyl-lower alkyl, cycloalkyl, lower alkoxycarbonyl, carboxy, phenyl, substituted phenyl, pyridinyl, pyrimidinyl or pyrazinyl;
$R_4$ represents hydrogen, lower alkyl or halogen;
or
(b) Py denotes 5-pyrimidyl, $R_1$ is hydrogen, $R_2$ is [[(3S)-3-(dimethylamino)-1-pyrrolidinyl]-methyl]-3-(trifluoromethyl)phenyl and $R_4$ is methyl;
or a pharmaceutically acceptable salt thereof, for the treatment of a proliferative disorder or other pathological conditions mediated by Bcr-Abl, c-Kit, DDR1, DDR2 or PDGF-R kinase activity, wherein the compound of formula (I) or a pharmaceutically acceptable salt thereof and, optionally, pharmaceutically acceptable carriers, are dispersed in a fruit preparation, Furthermore, the instant invention pertains to the use of a pyrimidylaminobenzamide of formula I

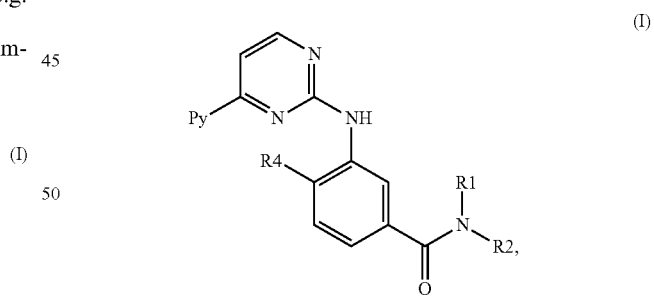

(I)

wherein
(a) Py denotes 3-pyridyl,
$R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; and R₃ represents hydroxy, lower alkoxy, acyloxy, carboxy, lower alkoxycarbonyl, carbamoyl, N-mono- or N,N-di-substituted carbamoyl, amino, mono- or di-substituted amino, cycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; or $R_1$ and $R_2$, together, represent alkylene with 4, 5 or 6 carbon atoms optionally mono- or di-substituted by lower alkyl, cycloalkyl, heterocyclyl, phenyl, hydroxy, lower alkoxy, amino, mono- or di-substituted amino, oxo, pyridyl, pyrazinyl or pyrimidinyl; benzalkylene with 4 or 5 carbon atoms; oxaalkylene with 1 oxygen and 3 or 4 carbon atoms; or azaalkylene with 1 nitrogen and 3 or 4 carbon atoms, wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-di-substituted carbamoyl-lower alkyl, cycloalkyl, lower alkoxycarbonyl, carboxy, phenyl, substituted phenyl, pyridinyl, pyrimidinyl or pyrazinyl;

$R_4$ represents hydrogen, lower alkyl or halogen;

or (b) Py denotes 5-pyrimidyl, $R_1$ is hydrogen, $R_2$ is [[(3S)-3-(dimethylamino)-1-pyrrolidinyl]-methyl]-3-(trifluoromethyl)phenyl and $R_4$ is methyl;

or a pharmaceutically acceptable salt thereof, for the manufacture of a medicament for the treatment of a proliferative disorder or other pathological conditions mediated by Bcr-Abl, c-Kit, DDR1, DDR2 or PDGF-R kinase activity, wherein the medicament is designated to be dispersed in a fruit preparation, optionally together with pharmaceutically acceptable carriers, and orally administered to a human patient in need thereof.

EXAMPLES

Example 1

In Vitro Stability Tests

The content of nilotinib capsules prepared as disclosed in WO2008/037716 is dispersed in yogurt or applesauce. It is shown that nilotinib is stable at room temperature for 15 minutes with mean nilotinib recovery between 97.6 to 99.9%.

Example 2

Randomized, Open Label, Three-Period Crossover Single-Center Study in 48 Healthy Subjects Comparing the Bioavailability of Nilotinib when Administered as Intact Capsule or the Capsule Content Mixed with Yogurt or Applesauce in Healthy Volunteers (HV)

The HV between 18 and 65 years obtain under fasted conditions either a single oral administration of 400 mg nilotinib with two intact 200 mg nilotinib capsules (treatment A); a single oral administration of 400 mg nilotinib with the content of two 200 mg nilotinib capsules each dispersed in one teaspoon of non-fat plain yogurt (treatment B); or a single oral administration of 400 mg nilotinib with the content of two 200 mg nilotinib capsules each dispersed in one teaspoon of applesauce (treatment C). Serial blood samples for serum nilotinib concentration determination are collected for up to 72 hous after each nilotinib administration. All treatments were administered with 240 mL of water, in the morning, after an overnight fast of at least 10 hours. Subjects continued to fast until 4 hours after administration. Standardized meals were served at 4 hours (lunch) and 10 hours (dinner) after nilotinib administration. Consumption of grapefruit, grapefruit juice, or any caffeinated beverages within 48 hours of study initiation was prohibited.

Serum nilotinib concentrations were determined from blood samples collected at pre-dose (0 hour) and 0.5, 1, 2, 3, 4, 5, 6, 8, 10, 12, 24, 36, 48, and 72 hours post-nilotinib administration on days 1, 13, and 25. At each time point, 2.5 mL of whole blood was drawn using a Serum Separator Vacutainer® (Becton, Dickinson and Company, Franklin Lakes, N.J., USA) tube. The tube was allowed to stand vertically at room temperature for 30 minutes prior to centrifugation at 5° C. for 10 minutes at 1100 g. Immediately after centrifugation, the upper serum sample was transferred and stored frozen at ≤−15° C. until shipped to the analytical site for sample analyses.

Serum concentrations of nilotinib were measured using a validated liquid chromatography-tandem mass spectrometry (LC-MS/MS) assay as described previously, with slight modifications (Larson R A, le Coutre P D, Reiffers J et al. J Clin Oncol 28:7s, 2010 (suppl; abstr 6501)). Nilotinib and the internal standard, [M+4]nilotinib, were extracted from a 100 μL serum sample with 700 μL of methyl tertiary-butyl ether (MTBE). The MTBE layer was transferred, evaporated to dryness, and reconstituted with 400 μl of an acetonitrile and 0.2% formic acid mixture (40:60, v/v). Chromatography was carried out using a Phenomenex Synergi™ Polar-RP column (particle size 4 μm, 50 mm×2 mm i.d.) (Phenomenex, Inc, Torrance, Calif.) held at room temperature. Elution of the analytes was performed using a isocratic elution at a flow rate of 0.5 mL/min with mobile phases of 0.2% formic acid in 10 mM aqueous ammonium formate: 0.2% formic acid in acetonitrile (60:40, v/v). Detection was performed by MS/MS in positive ion mode on a Sciex API4000 mass spectrometer (Applied Biosystem, USA) with multiple reaction monitoring of m/z 530→289 for nilotinib and 534→293 for the internal standard. The lower limit of quantification for nilotinib was 2.50 ng/mL using a 100 μL serum sample. Precision of the assay at each QC level was <11% and the accuracy ranged from 95.2% to 104.3%.

Following the administration of a single oral dose of 400-mg nilotinib as two 200-mg intact capsules, the peak serum concentration of nilotinib occurred at a median time ($t_{max}$) of 4.0 hours, and the $C_{max}$ values averaged 398 ng/mL. The mean $t_{1/2}$ of nilotinib was found to be 19.8 hours. These results are in agreement with those observed in previous studies in healthy volunteers who received a same 400-mg oral dose of nilotinib as intact capsules. Compared with the administration of 400-mg nilotinib as two 200-mg intact capsules (Treatment A), the systemic exposure of nilotinib was found to be generally higher following the administration of nilotinib as two capsule contents (400 mg) mixed with yogurt (Treatment B). The geometric mean values of $C_{max}$, $AUC_{a\text{-}tlast}$, and $AUC_{0\text{-}inf}$ of nilotinib were increased by 31%, 11%, and 8% respectively. The 90% Cls of the geometric mean ratio (Treatment B vs A) of nilotinib $C_{max}$, $AUC_{0\text{-}t}$ and $AUC_{0\text{-}\infty}$ were 1.22-1.41, 1.05-1.06, and 1.02-1.15, respectively.

Administration of the contents of two nilotinib capsules (400 mg) dispersed in applesauce (Treatment C), showed similar exposure compared with administration of nilotinib as intact capsules (Treatment A). The geometric mean ratio (Treatment C vs A) of nilotinib $C_{max}$, $AUC_{0\text{-}tlast}$, and $AUC_{0\text{-}inf}$ was 0.95, 0.99, and 0.97 respectively, and the corresponding 90% CIs were 0.88-1.02, 0.94-1.04, and 0.90-1.03 respectively.

The results are summarized in Table 1.

TABLE 1

Study Results

| PK Parameter | Geometric mean | | Ratio and 90% CIs B vs A |
|---|---|---|---|
| | Treatment A (intact capsule) | Treatment B (mixed with yogurt) | |
| Tmax (h) | 4.0 | 4.0 | −0.02 (−8.0, 6.0) |
| Cmax (ng/mL) | 398 | 525 | 1.31 (1.22-1.41) |
| AUC0-t (ng*h/mL) | 11 223 | 12 559 | 1.11 (1.05-1.16) |
| AUC0-∞ (ng*h/mL) | 11 965 | 13 655 | 1.08 (1.02-1.15) |
| $t_{1/2}$ (h) | 19.7 | 21.0 | NA |

| PK Parameter | Treatment A (intact capsule) | Treatment C (mixed with applesauce) | Ratio and 90% CIs C vs A |
|---|---|---|---|
| Tmax (h) | 4.0 | 3.0 | −0.02 (−6.00, 6.07) |
| Cmax (ng/mL) | 398 | 378 | 0.95 (0.88-1.02) |
| AUC0-t (ng*h/mL) | 11 223 | 11 214 | 0.99 (0.94-1.04) |
| AUC0-∞ (ng*h/mL) | 11 965 | 12 105 | 0.97 (0.90-1.03) |
| $t_{1/2}$ (h) | 19.7 | 20.6 | NA |

The studies allow the following conclusions:

Single oral administration of 400 mg nilotinib, with two 200 mg nilotinib capsules content, each dispersed in one teaspoon of non-fat plain yogurt is not bioequivalent to a single oral administration of 400 mg nilotinib given as intact capsules.

Single oral administration of 400 mg nilotinib, with two 200 mg nilotinib capsules content, each dispersed in one teaspoon of applesauce is bioequivalent to a single oral administration of 400 mg nilotinib given as intact capsules.

The studies also show that the administration of nilotinib in a fruit preparation is safe and well tolerated by human subjects.

We claim:

1. A method of treating a proliferative disorder wherein the proliferative disorder or other pathological condition is selected from melanoma, breast cancer, cancer of the colon, lung cancer, cancer of the prostate or Kaposi's sarcoma, gastrointestinal stromal tumors (GIST), acute myeloid leukemia (AML), leukemia which responds to an inhibition of the Abl tyrosine kinase activity, mesothelioma, systemic mastocytosis, hypereosinophilic syndrome (HES), fibrosis, rheumatoid arthritis, polyarthritis, scleroderma, lupus erythematosus, graft-versus host diseases, neurofibromatosis, pulmonary hypertension, Alzheimer's disease, seminomas and dysgerminomas and psoriasis comprising oral administration of an effective dose of a pyrimidylaminobenzamide of formula (I):

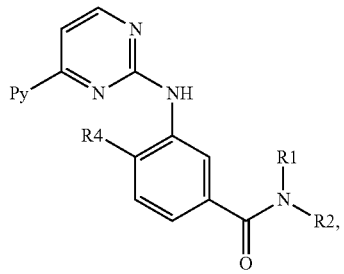

wherein
(a) Py denotes 3-pyridyl,
$R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; and
$R_3$ represents hydroxy, lower alkoxy, acyloxy, carboxy, lower alkoxycarbonyl, carbamoyl, N-mono- or N,N-di-substituted carbamoyl, amino, mono- or di-substituted amino, cycloalkyl, heterocyclyl, an aryl group, or a mono- or bi-cyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; or
$R_1$ and $R_2$, together, represent alkylene with 4, 5 or 6 carbon atoms optionally mono- or di-substituted by lower alkyl, cycloalkyl, heterocyclyl, phenyl, hydroxy, lower alkoxy, amino, mono- or di-substituted amino, oxo, pyridyl, pyrazinyl or pyrimidinyl; benzalkylene with 4 or 5 carbon atoms; oxaalkylene with 1 oxygen and 3 or 4 carbon atoms; or azaalkylene with 1 nitrogen and 3 or 4 carbon atoms, wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-di-substituted carbamoyl-lower alkyl, cycloalkyl, lower alkoxycarbonyl, carboxy, phenyl, substituted phenyl, pyridinyl, pyrimidinyl or pyrazinyl;
$R_4$ represents hydrogen, lower alkyl or halogen;
or
(b) Py denotes 5-pyrimidyl, $R_1$ is hydrogen, $R_2$ is [[(3S)-3-(dimethylamino)-1-pyrrolidinyl]methyl]-3-(trifluoromethyl)phenyl and $R_4$ is methyl;
or a pharmaceutically acceptable salt thereof, and, optionally, pharmaceutically acceptable carriers, dispersed in a fruit preparation, to a human patient in need thereof.

2. The method according to claim 1, wherein the pyrimidylaminobenzamide is 4-methyl-3-[[4-(3-pyridinyl)-2-pyrimidinyl]amino]-N-[5-(4-methyl-1H-imidazol-1-yl)-3-(trifluoromethyl)phenyl]benzamide.

3. The method according to claim 2, wherein the pyrimidylaminobenzamide is employed in the form of its hydrochloride monohydrate.

4. The method according to claim 1, wherein the human patient is an elderly or a pediatric patient.

5. The method according to claim 1, wherein the fruit preparation is a juice, sauce or puree prepared from fruits.

6. The method according to claim 1, wherein the fruit preparation is applesauce.

7. A commercial package containing a pyrimidylaminobenzamide of formula I

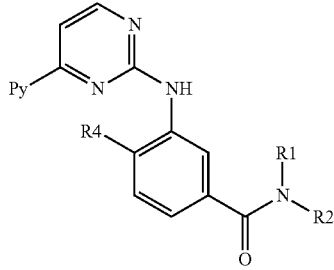

wherein
(a) Py denotes 3-pyridyl,
R₁ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
R₂ represents hydrogen, lower alkyl, optionally substituted by one or more identical or different radicals R₃, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; and
R₃ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;
or wherein R₁ and R₂ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;
R₄ represents hydrogen, lower alkyl, or halogen;
wherein the prefix "lower" denotes a radical having up to and including a maximum of 7 carbon atoms,
or
(b) Py denotes 5-pyrimidyl, R₁ is hydrogen, R₂ is [[(3S)-3-(dimethylamino)-1-pyrrolidinyl]methyl]-3-(trifluoromethyl)phenyl and R₄ is methyl;
or a pharmaceutically acceptable salt thereof, respectively, together with instructions to disperse the compound of formula I or a pharmaceutically acceptable salt thereof in a fruit preparation.

8. A pyrimidylaminobenzamide of formula I

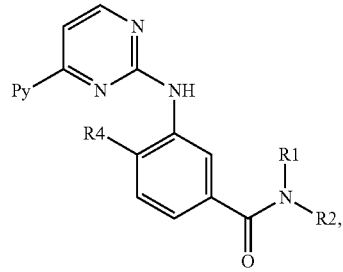

wherein
(a) Py denotes 3-pyridyl,
R₁ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
R₂ represents hydrogen, lower alkyl, optionally substituted by one or more identical or different radicals R₃, cycloalkyl, benzcycloalkyl, heterocyclyl, an aryl group, or a mono- or bicyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; and
R₃ represents hydroxy, lower alkoxy, acyloxy, carboxy, lower alkoxycarbonyl, carbamoyl, N-mono- or N,N-disubstituted carbamoyl, amino, mono- or di-substituted amino, cycloalkyl, heterocyclyl, an aryl group, or a mono- or bi-cyclic heteroaryl group comprising 0-, 1-, 2- or 3-ring nitrogen atoms and 0 or 1 oxygen atom and 0 or 1 sulfur atom, which groups in each case are unsubstituted or mono- or poly-substituted; or
R₁ and R₂, together, represent alkylene with 4, 5 or 6 carbon atoms optionally mono- or di-substituted by lower alkyl, cycloalkyl, heterocyclyl, phenyl, hydroxy, lower alkoxy, amino, mono- or di-substituted amino, oxo, pyridyl, pyrazinyl or pyrimidinyl; benzalkylene with 4 or 5 carbon atoms; oxaalkylene with 1 oxygen and 3 or 4 carbon atoms; or azaalkylene with 1 nitrogen and 3 or 4 carbon atoms, wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N, N-di-substituted carbamoyl-lower alkyl, cycloalkyl, lower alkoxycarbonyl, carboxy, phenyl, substituted phenyl, pyridinyl, pyrimidinyl or pyrazinyl;
R₄ represents hydrogen, lower alkyl or halogen;
or
(b) Py denotes 5-pyrimidyl, R₁ is hydrogen, R₂ is [[(3S)-3-(dimethylamino)-1-pyrrolidinyl]methyl]-3-(trifluoromethyl)phenyl and R₄ is methyl;
or a pharmaceutically acceptable salt thereof, for the treatment of a proliferative disorder wherein the proliferative disorder or other pathological condition is selected from melanoma, breast cancer, cancer of the colon, lung cancer, cancer of the prostate or Kaposi's sarcoma, gastrointestinal stromal tumors (GIST), acute myeloid leukemia (AML), leukemia which responds to an inhibition of the Abl tyrosine kinase activity, mesothelioma, systemic mastocytosis, hypereosinophilic syndrome (HES), fibrosis, rheumatoid arthritis, polyarthritis, scleroderma, lupus erythematosus, graft-versus host diseases, neurofibromatosis, pulmonary hypertension, Alzheimer's disease, seminomas and dysgerminomas and psoriasis wherein the compound of formula (I) or a pharmaceutically acceptable salt thereof and, optionally, pharmaceutically acceptable carriers, are dispersed in a fruit preparation.

* * * * *